United States Patent [19]

Chang

[11] Patent Number: 4,627,869

[45] Date of Patent: Dec. 9, 1986

[54] METHOD FOR INHIBITING AXILLARY BUD GROWTH

[75] Inventor: In-Kook Chang, Painesville, Ohio

[73] Assignee: SDS Biotech Corporation, Painesville, Ohio

[21] Appl. No.: 630,307

[22] Filed: Jul. 12, 1984

[51] Int. Cl.⁴ ............................................. A01N 37/10
[52] U.S. Cl. .......................................... 71/78; 71/112
[58] Field of Search ............................... 71/78, 84, 112

[56] References Cited

U.S. PATENT DOCUMENTS

| | | | |
|---|---|---|---|
| 2,923,634 | 2/1960 | Lindemann | 71/112 |
| 2,978,838 | 4/1961 | Beatty | 71/107 |
| 4,071,348 | 1/1978 | Abramitis | 71/78 |
| 4,094,664 | 6/1978 | Thomas | 71/78 |
| 4,124,370 | 11/1978 | Yu | 71/78 |

Primary Examiner—Glennon H. Hollrah
Attorney, Agent, or Firm—Thoburn T. Dunlap; John P. Hazzard

[57] ABSTRACT

A method for inhibiting bud growth and development on plants by applying to the plants a bud growth inhibiting amount of dimethyl 2,3,5,6-tetrachloroterephthalate is disclosed.

2 Claims, No Drawings

METHOD FOR INHIBITING AXILLARY BUD GROWTH

BACKGROUND OF THE INVENTION

1. Technical Field of the Invention

This invention relates to a method for controlling bud growth in plants. More particularly, this invention relates to the use of dimethyl 2,3,5,6-tetrachloroterephthalate for controlling the growth of axillary buds in tobacco plants.

2. Description of the Prior Art

Near maturity, the apically dominant terminal bud of the tobacco plant develops into a reproductive bud that eventually produces flowers. These flowers, if allowed to mature, develop into seed heads. As the seed heads mature, lateral buds develop in the leaf axils of the plant. These lateral or axillary buds (suckers) grow as vegetative shoots that eventually develop floral parts for reproduction. During this flowering and reproductive process, most of the plant's energy and nutritional resources are directed to its floral parts, diverting vital resources away from other plant tissues such as the leaves. This adversely affects the leaf tissue, reducing the size, yield and ultimately the quality of the tobacco leaf.

In the practice of tobacco production, the terminal bud is removed at or before the flowering stage; a practice known in the art as topping. Topping facilitates the development of a large tobacco leaf which is commercially desirable. However, removal of the terminal bud destroys apical dominance, resulting in the accelerated growth and development of the axillary buds. The uncontrolled growth and development of these suckers again reduces the nutrient supply available to the leaf tissue, consequently resulting in leaves of inferior quality and size. These suckers must be continuously removed to achieve the desired purpose of topping, i.e., improved size, yield, and leaf quality.

The earliest attempts for controlling sucker growth involved removal of the suckers from the tobacco plant by hand. Since the suckers were not all in the same developmental stage, the field had to be worked several times before complete control could be achieved. These manual methods were time consuming, laborious and expensive. A more efficient and cost effective means for controlling axillary bud growth was therefore needed. Several chemical growth controlling agents have been suggested and are in present day use.

In the practice of controlling axillary bud growth by chemical means, the tobacco plant is first topped to remove the terminal buds. Axillary bud development is then controlled by subsequently spraying the tobacco plant with a chemical growth controlling agent specific for the inhibition of axillary bud growth and development.

Among the most widely used chemical agents for tobacco sucker control is maleic hydrazide. Maleic hydrazide is a systemic type regulator that is readily translocated throughout the tobacco plant. This compound is active in meristematic tissues, i.e., bud tissues, of the plant, functioning as a cell division inhibitor. Both the timing of application and the environmental conditions are important for the maximum effectiveness of this compound. If applied too soon after topping, the compound can adversely affect the leaf expansion of developing tobacco leaves. If applied under low humidity conditions, the uptake of the compound can be severely curtailed. In addition, there have been some recent questions regarding the mammalian toxicology of the compound.

The $C_6$–$C_{12}$ saturated fatty alcohols have also found use as chemical sucker controlling agents. These compounds are contact type regulators that must directly contact each axillary bud in order to be effective. The fatty alcohols destroy the water retaining membrane of the axillary buds, resulting in complete desiccation of the bud tissue. However, the tobacco grower must pay particular attention when using these compounds, as too great a concentration of active compound can also affect the developing crop leaves.

Recently, the dinitroanilines have been found to be effective tobacco sucker controlling agents as disclosed in U.S. Pat. Nos. 3,880,645; 4,046,809 and 4,123,250. The dinitroanilines are contact-local-systemic agents, inhibiting localized cell divisions in the meristematic tissues. Again, this type of agent must be applied at the correct time, i.e., after the young leaves of the tobacco plant have sufficiently developed, or malformation of the desired crop leaves may subsequently occur, reducing the crop yield and marketability of the leaves.

It would, therefore, be desirable to provide an axillary bud controlling agent that exhibits good efficacy while not causing injury to the developing crop. Accordingly, it is an object of the present invention to provide a chemical method for inhibiting bud growth on plants without adversely affecting the desirable portions thereof.

Another object is to provide a chemical composition which is economical to produce and use, and safe to handle. Other objects and advantages of the present invention will become apparent from the description of the invention which follows.

SUMMARY OF THE INVENTION

It has now been discovered in accordance with the present invention that dimethyl 2,3,5,6-tetrachloroterephthalate (DCPA) is an effective agent for the control of bud growth on plants.

Further in accordance with the present invention, DCPA controls axillary bud growth without adversely affecting the desired portions of the treated plant.

Still further in accordance with the present invention a method is provided for controlling the axillary bud growth and development on tobacco plants which comprises applying to tobacco plants whose axillary bud growth is to be controlled a composition containing an effective amount of DCPA.

DESCRIPTION OF THE PREFERRED EMBODIMENTS

DCPA, used in the practice of the method of the present invention, is generally a known compound. It is presently known that certain dimethyl tetrahaloterephthalates possess herbicidal activity. U.S. Pat. No. 2,923,634 discloses the use of these compounds, particularly dimethyl 2,3,5,6-tetrachloroterephthalate, to kill weeds, such use being characterized by selective preemergent herbicidal activity. This patent, however, does not disclose the use of the dimethyl tetrahaloterephthalates, and in particular, dimethyl 2,3,5,6,-tetrachloroterephthalate used in accordance with the present invention to control bud growth in plants. Further, this patent does not disclose the use of dimethyl 2,3,5,6-tetrachloroterephthalate for the control of axillary bud growth in tobacco plants.

DCPA may be readily prepared by conventional synthesis methods well known in the art. N. Rabjohn in the "Journal of the American Chemical Society," Vol. 70, page 3518 (1948) describes a method for synthesizing dimethyl 2,3,5,6-tetrachloroterephthalate by chlorinating terephthalyl dichloride and reacting the resultant tetrachloroterephthalyl dichloride with methanol, preferably at reflux. The product may be purified by recrystallization from an organic solvent if desired. Other preparative and recovery methods are disclosed in U.S. Pat. Nos. 3,052,712 and 3,402,195 which are herein incorporated by reference.

In using DCPA as a chemical axillary bud controlling agent, the compound may be applied to plants in the form of solutions, emulsions, suspensions, dispersions and the like. DCPA may initially be formulated as a concentrate in a liquid or solid carrier which may be further mixed with a suitable diluent or application vehicle to provide the requisite field rate.

Useful liquid carriers in which DCPA may be dissolved, suspended or dispersed include, for example, aromatic hydrocarbons (e.g., benzene, toluene, xylene, etc.), halogenated aromatic hydrocarbons (e.g., chlorobenzenes), paraffins (e.g., petroleum fractions), chlorinated aliphatic hydrocarbons (e.g., methylene chloride, etc.) alcohols (e.g., methanol, ethanol, propanol, butanol, etc.), ethers and ether alcohols (e.g., glycol, glycol monomethyl ether, etc.), amines (e.g., ethanolamine, etc.), amides (e.g., dimethylformamide, etc.), ketones (e.g., acetone, methyl ethyl ketone, etc.) as well as other conventional solvents.

Suitable solid carriers in which the compound of the present invention may be dispersed, include, for example, attaclay, kaolin, alumina, silica, calcium carbonate, kieselguhr (diatomaceous earth) and talc. The dry compositions are typically formulated as wettable powders and applied as sprays using water as an application vehicle.

The formulations are prepared in the conventional manner, for example, by diluting the active ingredient with the foregoing solvents or carriers with or without the addition of nonionic and anionic emulsifying agents or surface active agents (e.g., polyethylene oxide esters of fatty acids, fatty alcohols, alkyl sulfonates, aryl sulfonates, etc.) and dispersants (e.g., lignan, sulfite waste liquors, methylcellulose, etc.) As employed typically in the methods of the present invention, such formulations may contain from about 0.01 percent to about 99 percent, by weight of the active compound.

The compositions, if desired, may be formulated with other compatible insecticides, fungicides and the like. DCPA may also be formulated with other tobacco axillary bud growth inhibiting agents to form combination products useful in the method of the present invention.

The composition is preferably used at a rate from about 6 to about 600 mg of active material per tobacco plant. Greater or lesser amounts may, of course be employed depending upon the degree of control which is desired.

The composition employed in the method of this invention is preferably applied as a directed foliar spray or it may be applied directly to the locus, i.e., the axillary buds to be treated. When the composition in the method of this invention is applied as a directed foliar spray, an effective volume of application must be employed to allow the spray to run down the stem so that the active ingredient may contact the axillary buds. The composition may also be applied as a multiple or a sequential application. As used herein, a multiple application refers to two or more separate applications of DCPA usually spaced 3-10 days apart. A sequential application refers to an application of DCPA followed by an application of a compatible axillary bud controlling agent 5-14 days later. Alternately, the compatible axillary bud controlling agent may be applied first followed by an application of DCPA. Compatible tobacco axillary bud controlling agents contemplated for use are, for example, the $C_6$-$C_{12}$ fatty alcohols and maleic hydrazide.

The composition is preferably applied to tobacco which has been topped at or before the late button stage of tobacco development and before the new suckers are more than about 2.5 cm long.

Various features and aspects of the present invention will be further illustrated in the examples that follow. These examples should not be considered, however, as a limitation upon the scope of this invention.

GREENHOUSE TESTING

Example 1

Greenhouse grown tobacco plants, Flue-Cured type (variety Coker 319), were topped at the early flower stage. Top primary suckers were allowed to attain a length of 2-5 cm. Four days after topping, a 6 percent EC (emulsifiable concentrate) formulation, diluted to contain the amounts of DCPA indicated in Table I, was sprayed onto the center of each plant (10 ml of test formulation) so that the formulation would run down the tobacco stalk and contact each sucker. After being sprayed, the plants were placed at random on a greenhouse bench and watered normally for a period of 31 days. At the conclusion of the test, the degree of sucker control was determined by counting and weighing the fresh weight of the suckers from each treated plant. The results are expressed as the percent sucker control compared with the fresh weight of suckers from untreated but topped control plants.

Percent sucker control was calculated by the formula:

$$\% \text{ control} = \frac{TNS - TR + /TNS - TR/}{2TNS} \times 100$$

where TNS is the fresh weight of suckers of the untreated tipped control and TR is the fresh weight of the suckers of the treated plants. The results are set forth in Table I. All numbers expressed represent an average of two replications.

TABLE I

| Treatment* (mg a.i./Plant) | No. of Suckers Per Plant | Sucker Fresh Wt. Per Plant (g) | Percent Control |
|---|---|---|---|
| DCPA | | | |
| 6 | 2 | 233 | 38 |
| 12 | 1.5 | 15 | 96 |
| 24 | 0 | 0 | 100 |
| Rate Equivalent of EC base (Blank) | | | |
| 6 | 5 | 353 | — |
| 12 | 5 | 332 | — |
| 24 | 6 | 313 | — |
| Untreated | 5 | 376 | — |

TABLE I-continued

| Treatment* (mg a.i./Plant) | No. of Suckers Per Plant | Sucker Fresh Wt. Per Plant (g) | Percent Control |
| --- | --- | --- | --- |
| Topped Control | | | |

*a.i. = active ingredient.

Example 2

The following example demonstrates the duration of sucker control exhibited by DCPA.

Greenhouse grown tobacco plants, Flue-Cured type (variety Coker 319), were topped and treated as in Example 1. A 24 percent OBF (oil-based flowable) formulation of DCPA was sprayed onto each plant at the rates indicated in Table II. After being sprayed, the plants were placed at random on a greenhouse bench and watered normally for a period of 8 to 9 weeks. A sequential treatment comprising maleic hydrazide (MH-30) and a combination of fatty alcohols (OFF-SHOOT-T sold by the Proctor & Gamble Co., Cincinnati, Ohio) having the following composition by weight of $C_6$ to $C_{12}$ saturated fatty alcohols: $C_6$-0.5%; $C_8$-42%; $C_{10}$-56%; and $C_{12}$-1.5% was included for comparison. The percent control was calculated as in Example 1. Visual evaluations of the duration of sucker control were made weekly until the sucker control for a particular treatment broke, i.e., when new suckers grew out from the majority of the plants. The results are set forth in Table 2.

TABLE II

| Treatments (mg a.i./Plant) | No. of Suckers Plant | Sucker Fresh Wt. per Plant (g) | Percent Control | Duration of Control (Wks) |
| --- | --- | --- | --- | --- |
| DCPA | | | | |
| 24 | 0.5 | 117 | 69 | <8 |
| 48 | 0.5 | 9 | 99 | 9 |
| 96 | 0 | 0 | 100 | >9 |
| *Fatty alcohol mixture/Maleic hydrazide 4% (v/v)/81 | 1 | 12 | 98 | 8 |
| Untreated Topped Control | 6 | 759 | — | 8 |

*The maleic hydrazide was applied 7 days after the application of the fatty alcohol mixture.

Example 3

Greenhouse grown Burley type (variety Kentucky 14) tobacco plants were topped and treated as in Example 1. EC and OBF formulations containing DCPA were sprayed at the rates indicated in Table III. After being sprayed, the plants were placed at random on a greehouse bench and watered normally for a period of 5 weeks. Maleic hydrazide and a fatty alcohol mixture (Off-Shoot-T) were included for comparison. Percent control was calculated as in Example 1. The results are set forth in Table III.

TABLE III

| Treatment (mg a.i./Plant) | No. of Suckers Per Plant | Sucker Fresh Wt. Per Plant (g) | Percent Control |
| --- | --- | --- | --- |
| DCPA EC | | | |
| 12 | 2 | 145 | 67 |
| 18 | 1 | 33 | 93 |

TABLE III-continued

| Treatment (mg a.i./Plant) | No. of Suckers Per Plant | Sucker Fresh Wt. Per Plant (g) | Percent Control |
| --- | --- | --- | --- |
| 24 | 0.5 | 86 | 81 |
| DCPA OBF | | | |
| 48 | 0 | 0 | 100 |
| 96 | 0 | 0 | 100 |
| Maleic Hydrazide | | | |
| 48 | 4 | 127 | 71 |
| 96 | 1 | 8 | 98 |
| Fatty Alcohol mixture 4% (V/V) | 3.5 | 304 | 32 |
| Untreated Topped Control | 5.5 | 445 | — |

Example 4

Adverse side effects caused by sucker controlling agents, such as necrosis and leaf malformation on harvestable leaves, lower the quality of cured leaves and reduces crop yields. In the following example DCPA was compared to an untreated control for incidence of adverse side effects. Several commercial standards were included for comparison. The commercial standards employed were: the potassium salt of maleic hydrazide (ROYAL MH-30 sold by Uniroyal, Inc., Naugatuck, Conn.); 2-chloro-N-[2,6-dinitro-4-(trifluoromethyl)-phenyl]-N-ethyl-6-fluorobenzenemethanamine 1.21 lbs. a.i/gal. EC (PRIME+sold by Ciba-Geigy Corp., Greensboro, N.C.); and Off-Shoot-T.

Greenhouse grown Flue-Cured (variety Coker 319) tobacco plants were topped in the button stage of development. Immediately after topping, 10 ml of each test formulation was sprayed onto respective plants. Three chemicals were applied as a coarse spray; maleic hydrazide, as a fine spray. After being sprayed, the plants were placed at random on a greenhouse bench and watered normally for a period of 20 days. At the termination of the test, leaf fresh weight, necrosis and malformation were evaluated using the following rating system:

Leaf FW=fresh weight of the 2 topmost leaves per plant.
Leaf Nec.=necrotic spots and leaf burn of topmost third of all leaves on plant.
Ratings: 0—none; 1—very slight; 2—slight; 3—moderate; 4—severe; 5—very severe.
Leaf Malf.=malformation of topmost 2 leaves of plant.
Ratings: 0—none; 1—very slight; 2—slight; 3—moderate; 4—severe; 5—very severe.
Test results are expressed in Table IV. Results are the average of 4 replications.

TABLE IV

| Treatment (mg a.i./Plant) | | Leaf Malf. (0–5) | Leaf Nec. (0–5) | Leaf FW (g) |
| --- | --- | --- | --- | --- |
| DCPA* | 24 | 0.25 | 0 | 62 |
| Fatty Alcohol mixture 4% (V/V) | | 1.75 | 1.5 | 59 |
| Maleic Hydrazide | 48 | 2.25 | 2.25 | 59 |
| 2-chloro-N—[2,6-dinitro-4-(trifluoromethyl)phenyl]-N—ethyl-6-fluorobenzene- | 24 | 2.75 | 0 | 42 |

TABLE IV-continued

| Treatment (mg a.i./Plant) | Leaf Malf. (0–5) | Leaf Nec. (0–5) | Leaf FW (g) |
|---|---|---|---|
| methanamine | | | |
| Untreated topped Control | — | 0 | 0 | 31 |

*Wettable powder formulation suspended in an anionic surfactant solution.

Example 5

This example demonstrates the ability of DCPA to control the axillary bud growth on tomato plants.

Greenhouse grown tomato plants (variety Beefsteak) were treated with DCPA at the rates indicated in Table V (2 replications per treatment). Each axillary bud was individually treated at an application volume of 100 μl. The plants were treated at the early flowering stage, i.e., opening of the first flower buds. After being treated the plants were placed at random on a greenhouse bench and watered normally for a period of 4 weeks. At the termination of the test, the percent sucker control was calculated as in Example 1. The results are set forth below.

TABLE V

| Treatment | Rates (μg a.i./Axillary Bud) | No. of Suckers Per Plant | Sucker Fresh Wt. Per Plant (g) | Percent Control |
|---|---|---|---|---|
| DCPA 6% EC | 30 | 7 | 100.3 | |
| | | 7 | 108.9 | 28 |
| | 60 | 8 | 135.5 | |
| | | 5 | 87.3 | 23 |
| | 120 | 5 | 119.5 | |
| | | 6 | 119.1 | 17 |
| | 480 | 2 | 4.9 | |
| | | 0 | 0.0 | 98 |
| DCPA 24% OBF | 60 | 6 | 88.6 | |
| | | 4 | 95.2 | 36 |
| | 120 | 6 | 87.2 | |
| | | 7 | 115.7 | 30 |
| | 240 | 7 | 135.7 | |
| | | 5 | 73.4 | 28 |
| | 960 | 2 | 2.0 | |
| | | 1 | 1.1 | 99 |
| Control | — | 10 | 136.1 | — |
| | | 7 | 153.3 | — |

FIELD TESTING

Example 6

A field trial was conducted to determine the effects of DCPA on Flue Cured type (variety Coker 319) tobacco. The plants were topped in the button to early flowering stages of development, removing all top growth and leaving 18 to 20 harvestable leaves per plant. All suckers that were larger than 2.5 cm were removed by hand before spraying. A multiple application of DCPA (the first application was made immediately after topping; the second, 7 days later) was made to the tobacco plants.

Five to 10 plants per plot with 4 replications per treatment were sprayed on a broadcast basis at a spray volume of 50 gal. per acre. The test formulations were sprayed on the center of each row so that the formulation would flow along the tobacco stalk and contact each sucker.

A 75 percent WP (wettable powder) formulation of DCPA was employed at the rates indicated at Table VI. A sequential application of Off-Shoot-T (applied immediately after topping) and maleic hydrazide (applied 7 days later) and a single application of 2-chloro-N-[2,6-dinitro-4-(trifluoromethyl)phenyl]-N-ethyl-6-fluorobenzenemethanamine were sprayed for comparative purposes. Evaluations were conducted 6 weeks after the initial treatment. The results are given below in Table VI.

TABLE VI

| Treatments | Rates (lbs. a.i./A) 1st | 2nd | No. of Suckers Per Plant | Percent Control |
|---|---|---|---|---|
| DCPA | 1.0 | 1.0 | 1.6 | 83 |
| | 1.0 | 3.0 | 0.4 | 95 |
| | 2.0 | 2.0 | 0.7 | 93 |
| | 1.5 | 3.0 | 0.8 | 97 |
| | 4.0 | 4.0 | 0.3 | 95 |
| Fatty alcohol mixture/ maleic hydrazide | 12.0 | 2.25 | 4.6 | 75 |
| 2-chloro-N—[2,6-dinitro-4-(trifluoromethyl)phenyl]-N—ethyl-6-fluoro-benzenemethanamine | 1.25 | — | 0.1 | 96 |
| Control | — | — | 6.9 | — |

Example 7

Responses of Burley type (hybrid type MS by 21× Ky 10 and Kentucky 14) tobacco to DCPA were studied in areas where a typical Burley type tobacco culture is made. The plants were topped and treated as in Example 5. Evaluations were conducted 25 to 35 days after the initial treatment. The results illustrated below are an average from two test locations.

TABLE VII

| | Treatment (lb a.i./A) 1st | 2nd | No. of Suckers Per Plant | Percent Control |
|---|---|---|---|---|
| DCPA | 3 | — | 0.8 | 91 |
| | 3 | 3 | 0.1 | 99 |
| Fatty Alcohol Mixture | 12 | 12 | 2.7 | 73 |
| Maleic Hydrazide | 3 | — | 4.5 | 78 |

What is claimed is:

1. A method for inhibiting the growth and development of buds on plants, which method comprises contacting the plant with an effective amount of dimethyl 2,3,5,6-tetrachloroterephthalate.

2. A method for inhibiting the growth and development of axillary buds on tobacco plants, which method comprises contacting the tobacco plant with an effective amount of dimethyl 2,3,5,6-tetrachloroterephthalate.

* * * * *